United States Patent [19]

Kari et al.

[11] Patent Number: 5,153,311
[45] Date of Patent: Oct. 6, 1992

[54] IMMUNOGENIC GLYCOPROTEINS OF HUMAN CYTOMEGALOVIRUS GCII

[75] Inventors: Bruce E. Kari, Minneapolis; Richard C. Gehrz, Mendota Heights, both of Minn.

[73] Assignee: The Children's Hospital, Incorporated, St. Paul, Minn.

[21] Appl. No.: 227,622

[22] Filed: Aug. 3, 1988

Related U.S. Application Data

[63] Continuation-in-part of Ser. No. 158,389, Feb. 22, 1988, abandoned, which is a continuation-in-part of Ser. No. 933,789, Nov. 24, 1986, abandoned.

[51] Int. Cl.$^5$ ..................... C07K 15/04; C07K 15/14
[52] U.S. Cl. ..................... 530/395; 514/8; 424/88; 424/89
[58] Field of Search ............. 514/8; 530/395; 424/88, 424/89

[56] References Cited

U.S. PATENT DOCUMENTS

| | | | |
|---|---|---|---|
| 3,959,466 | 5/1976 | Plotkin | 424/89 |
| 4,680,338 | 7/1987 | Sundoro | 525/54.1 |
| 4,689,225 | 8/1987 | Pereira | 424/89 |
| 4,716,104 | 12/1987 | Harris et al. | 435/5 |
| 4,743,562 | 5/1988 | Rasmussen et al. | 435/518 |
| 4,783,399 | 11/1988 | Oldstone et al. | 435/5 |
| 4,818,678 | 4/1989 | Oldstone et al. | 435/5 |

FOREIGN PATENT DOCUMENTS

| | | |
|---|---|---|
| 0122841 | 10/1984 | European Pat. Off. |
| 0162533 | 11/1985 | European Pat. Off. |
| 0173177 | 3/1986 | European Pat. Off. |
| 0236145 | 9/1987 | European Pat. Off. |
| 0248909 | 12/1987 | European Pat. Off. |
| 0252302 | 1/1988 | European Pat. Off. |
| 0267014 | 5/1988 | European Pat. Off. |
| 0268014 | 5/1988 | European Pat. Off. |
| 85/05123 | 11/1985 | PCT Int'l Appl. |
| 88/03952 | 6/1988 | PCT Int'l Appl. |

OTHER PUBLICATIONS

G. H. Farrar et al., *J. Gen. Virol.*, 65, 1991–2001 (1984).
B. Nowak et al., *Virology*, 132, 325–338 (1984),
G. Farrar et al., *J. Gen. Virol.*, 67, 1469–1473 (1986).
K. M. Law et al., *J. of Med. Virol.*, 17, 255–266 (1985).
L. Rasmussen et al., *J. Virol.*, 55, 274–280 (1985).
B. Kari et al., *J. Virol.*, 60, 345–352 (1986).
W. J. Britt et al., *J. Virol.*, 58, 185 (1986).
W. J. Britt et al., *Virology*, 135, 369–378 (1984).
W. J. Britt et al., *Virus Research*, 4, 31–36 (1985).
B. R. Clark et al., *J. Virology*, 49, 279–282 (1984).
F. R. Cockerill III, *Mayo. Clin. Proc.*, 60, 636–637 (1985).
M. P. Cranage et al., *EMBO J.*, 5, 3057–3063 (1986).
T. Furukawa et al., *Proc. Soc. Exp. Biol. Med.*, 175, 243–250 (1984).
D. R. Gretch et al., *J. Virology*, 62, 875–881 (Mar., 1988).
G. M. Keil et al., *J. Virol.*, 61, 526–533 (1987).
K. S. Kim et al., *J. Clin. Microbiology*, 18, 331–343 (1983).
K. S. Kim et al., *J. Virol.*, 20, 604–611 (1976).
M. Mach et al., *J. Gen. Virol.*, 67, 1461–1467 (1986).
B. Nowak et al., *Virology*, 134, 91–102 (1984).
L. Pereira et al., *Infection and Immunity*, 36, 924–932 (1982).
L. Pereira et al., *Virology*, 139, 73–86 (1984).
L. E. Rasmussen et al., *Proc. Nat'l Acad. Sci. USA*, 81, 876–880 (1984).
M. F. Stinski, *J. Virol.*, 26, 686–701 (1978).
J. B. Britt et al., *Virology*, 135, 369–378 (1984).
L. Rasmussen et al., *J. Virol.*, 55, 274–280 (1985).
G. Farrar et al., *J. Gen. Virol.*, 67, 1469–1473 (1986).
B. Kari et al., *J. Virol.*, 60, 345–352 (1986).
D. R. Gretch et al., *J. Virol.*, 62, 875–881 (Mar., 1988).

(List continued on next page.)

*Primary Examiner*—David L. Lacey
*Assistant Examiner*—Shelly J. Guest
*Attorney, Agent, or Firm*—Merchant, Gould, Smith, Edell, Welter & Schmidt

[57] ABSTRACT

Substantially-pure immunogenic glycoprotein complexes of the gCII family, and constituent glycoproteins which can be derived from the membrane envelope of human cytomegalovirus are provided.

9 Claims, 2 Drawing Sheets

OTHER PUBLICATIONS

M. P. Cranage et al., *EMBO J.*, 5, 3057–3063 (1986).
N. O. Lussenhop et al., *Virology*, 164, 362–372 (1988).
L. Rasmussen et al., *Virology*, 163, 308–318 (1988).
Y. N. Liu, *J. Virol.*, 62, 1066–1070 (Mar., 1988).
F. X. Heinz et al., *Virology*, 130, 485–501 (1983).
A. Pinter et al., *Virology*, 116, 499–516 (1982).
R. J. Eisenberg et al., *J. Virol.*, 41, 478–488 (1982).
Juarez-Salinas et al., *Biotechniques*, 2, 164 (1984).
D. R. Gretch et al., *Anal. Biochem.*, 163, 270–277 (1987).
S. Alexander et al., *Science*, 266, 1328–1330 (1984).
J. Caust et al., *Arch. Virol.*, 96, 123–134 (1987).
H. Iwase, *Int. J. Biochem.*, 20, 479–491 (1988).
W. J. Britt et al., *J. Virol.*, 58, 185–191 (1986).
W. J. Britt et al., *Virus Research*, 4, 31–36 (1985).
B. R. Clark et al., *J. Virology*, 49, 279–282 (1984).
F. R. Cockerill III, *Mayo. Clin. Proc.*, 60, 636–638 (1985).
T. Furukawa et al., *Proc. Soc. Exp. Biol. Med.*, 175, 243–250 (1984).
G. M. Keil et al., *J. Virol.*, 61, 526–533 (1987).
B. Kari et al., *Biological Abstracts*, 83, No. 24219 (1987).
K. S. Kim et al., *Journal of Clinical Microbiology*, 18, 331–343 (1983).
K. S. Kim et al., *J. Virol.*, 20, 604–611 (1976).
K. M. Law et al., *Journal of Medical Virol.*, 17, 255–266 (1985).
M. Mach et al., *J. Gen. Virol.*, 67, 1461–1467 (1986).
Y. Masuho et al., *Biological Abstracts*, 84, No. 35910 (1987).
B. Nowak et al., *Virology*, 132, 325–338 (1984).
B. Nowak et al., *Virology*, 134, 91–102 (1984).
L. Pereira et al., *Infection and Immunity*, 36, 924–932 (1982).
L. Pereira et al., *Virology*, 139, 73–86 (1984).
L. Rasmussen et al., *Biological Abstracts*, 80, No. 100801 (1985).
L. E. Rasmussen et al., *Proc. Nat'l Acad. Sci. USA*, 81, 876–880 (1984).
M. F. Stinski, *J. Virol.*, 26, 686–701 (1978).

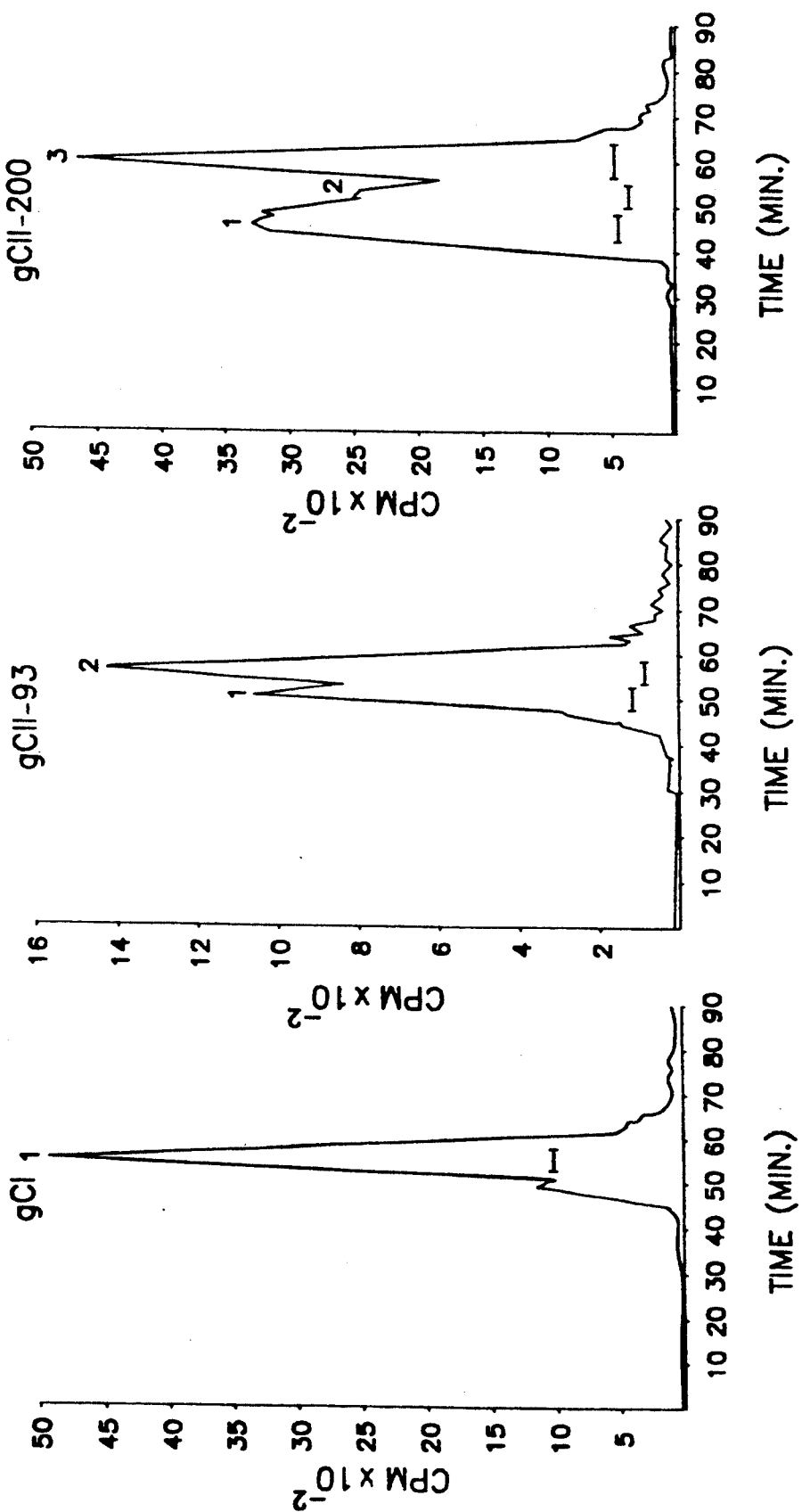

IMMUNOGENIC GLYCOPROTEINS OF HUMAN CYTOMEGALOVIRUS GCII

STATEMENT REGARDING FEDERALLY FUNDED SPONSORED RESEARCH

This invention was made with government support from the Department of Health and Human Services, Grant Number: HDMC 5 P01 HD19937-03 GT. The government may have certain rights in the invention.

CROSS-REFERENCE TO RELATED APPLICATION

This application is a continuation-in-part of U.S. application Ser. No. 158,389, filed Feb. 22, 1988, now abandoned, which in turn is a continuation-in-part of U.S. application Ser. No. 933,789, filed Nov. 24, 1986, now abandoned.

BACKGROUND OF THE INVENTION

The number of individual glycoproteins reported to be present in extracellular human cytomegalovirus (HCMV) has varied. Furthermore, little detailed information has been reported on the interactions and composition of HCMV glycoproteins. HCMV glycoproteins appear to be involved in human immune recognition of the virus. This has been demonstrated by the reactivity of HCMV glycoproteins with human convalescent sera. (G. H. Farrar et al., *J. Gen. Virol.*, 65, 1991 (1984); B. Nowak et al., *Virology*, 132, 325 (1984)). Biochemical approaches have been used to try to determine the number and composition HCMV glycoproteins. Farrar et al., cited above, were able to detect five polypeptides in the membranes of HCMV strain AD169 which were labeled by carbohydrate-specific methods. These glycoproteins had molecular weights ranging from 57,000 to 250,000. One method they employed labeled galactose (Gal) and/or N-acetylgalactosamine (GalNAc) residues. With this method, two glycoproteins with molecular weights of 67,000 and 130,000 showed relatively high incorporation of label suggesting that these glycoproteins have a distinct phenotype marked by relatively high concentrations of Gal and/or GalNAc and possibly high amounts of O-linked oligosaccharides.

Immunological approaches have also been used to try and identify the number of glycoproteins in HCMV. Several laboratories have generated monoclonal antibodies which recognize one or more disulfide-linked glycoprotein complexes which contain three individual glycoproteins. Several laboratories have reported molecular weights of 130,000, 92-95,000, and 52-55,000 for these glycoproteins (G. Farrar et al., *J. Gen. Virol.*, 67, 1469 (1986); B. E. Kari et al., *J. Virol.*, 60, 345 (1986); K. M. Law et al., *J. Med. Virol.*, 17, 255 (1985); L. Rasmussen et al., *J. Virol.*, 55, 275 (1985)). Kari et al. have disclosed two monoclonal antibodies (41C2 and 9B7) which recognize these glycoproteins. Hereinafter, the parent glycoprotein complex will be referred to as gCI. However, a continuing need exists to identify and characterize HCMV glycoprotein complexes and their constituent glycoproteins ("glycopeptides"), particularly those which can elicit a protective immune response.

BRIEF DESCRIPTION OF THE INVENTION

The present invention is directed to compositions of matter which are substantially-pure glycoprotein complexes or glycoproteins which can be derived from the HCMV gCII family of glycoprotein complexes. These compounds are found on the membrane envelope of the intact HCMV virion, where the glycoproteins are associated via disulfide linkages into the glycoprotein complexes. The glycoprotein complexes and their component glycoproteins are physically accessible to the immune system and to antibodies, and are capable of stimulating both humoral and cellular immunity in humans and in other mammals.

Therefore, one embodiment of the present invention is directed to substantially-pure, immunogenic glycoprotein complexes, which are on the membrane envelope of HCMV, wherein said complexes comprise an about 50–52 kD glycoprotein which reacts with the monoclonal antibody 9E10 produced by hybridoma ATCC HB 10926. Two of these complexes have a molecular weight of greater than about 200 kD or about 93 kD. Hereinafter, these complexes will be referred to as gCII-200 and gCII-93, respectively.

The present invention also is directed to substantially-pure, immunogenic HCMV envelope glycoproteins obtained by the purification of gCII, gCII-93 and/or gCII-200 following reduction. One of these glycoproteins has a molecular weight of about 50–52 kD, wherein said glycoprotein is on the membrane envelope of HCMV and is associated with other envelope glycoproteins by means of disulfide bonds, and wherein said glycoprotein reacts with the monoclonal antibody 9E10. Hereinafter, this glycoprotein will be referred to gp52(II). Glycoprotein gp52(II) can be prepared from either gCII-93 or gCII-200 by subjecting them to gelfiltration HPLC under reducing conditions. The present invention also is directed to two additional substantially-pure immunogenic glycoproteins, designated gp90(II) and gp200(II), which can be isolated from gCII, or preferably from gCII-200, under reducing conditions. These glycoproteins are also associated with other HCMV envelope glycoproteins by disulfide bonds. It was unexpectedly found that these glycoproteins react strongly with a novel class of monoclonal antibodies raised against gCII. These monoclonal antibodies, exemplified by 12G9, 14F9 and 15F9 (produced by hybridoma ATCC HB 10930), can be used to immunopurify gCII and can also react with gp90(II) and gp200(II) directly from reduced gCII in Western blot analysis.

This class of hybridomas and the monoclonal antibodies produced thereby differ from hybridoma ATCC HB 10926 and 9E10 in several respects: (a) the monoclonal antibodies, such as 15F9, react more strongly with gp90(II) and gp200(II) than with gp50–52(II); (b) the monoclonal antibodies recognize HCMV AD169, Toledo and Towne strains, but do not cross-react with HSV or adenovirus, whereas 9E10 recognizes HCMV Towne and Toledo, but not the AD169 strain, and also cross-reacts with HSV and adenovirus; and (c) the monoclonal antibodies are chemically stable, and therefore useful for immunopurification of gCII and gCII-200, e.g., by affinity chromatography, but do not react with gCII-93. Monoclonal antibody 9E10 will react with both gCII-93 and gCII-200 but is not stable under standard affinity chromatography conditions. Therefore, these new gcII-specific hybridomas and the monoclonal antibodies produced thereby are also within the scope of the present invention, as is their use to purify gCII-200 as well as glycoprotein complexes and reduced glycoproteins derived therefrom.

Due to their immunogenic properties, the present invention also provides a vaccine comprising an amount of one or more of these glycoproteins which is effective to produce an immune response against HCMV in a mammal, when administered thereto, in combination with a pharmaceutically-effective vehicle such as a liquid carrier. The gCII proteins are immunogenic in mice, rabbits and humans. For example, both gp90(II) and gp200(II) elicit strong B-cell immune responses when contacted with the blood of HCMV seropositive human donors. For a description of a vaccine employing gCI ("glycoprotein A") of HCMV, see L. Pereira (U.S. Pat. No. 4,689,225), the disclosure of which is incorporated by reference herein.

Apart from their use in vaccines, the present compositions are useful in the production of monoclonal antibodies, such as the new gCII-specific monoclonal antibodies described above, which in turn can be used to diagnose HCMV, or to treat HCMV infections by blocking HCMV infectivity and/or toxicity. The present compositions are also useful to produce clonal populations of antigen-specific T-helper lymphocytes, which in turn can be used for HCMV therapy.

To prepare the compositions of the present invention, several disulfide-linked glycoprotein complexes were extracted from human cytomegalovirus with a nonionic detergent and separated by anion exchange high performance liquid chromatography (HPLC). One complex had a molecular weight of 93,000 and was designated as gCII-93. Another related complex had a molecular weight greater than 200,000 and was designated as gCII-200. Both complexes were immunoprecipitated with monoclonal antibody 9E10, while gCII-200 was strongly immunoprecipitated by monoclonal antibody 15F9. A second group of complexes (classified as gCI) was immunoprecipitated with another monoclonal antibody (41C2).

The isolated complexes were reduced, alkylated, and the individual glycoproteins were separated by gel-filtration HPLC. Glycoproteins gp90(II), gp200(II) and gp52(II) were isolated from gCII-200 in this manner. Only a small amount of gp90(II) could be isolated from gCII-93, relative to the amount of gp52(II).

Glycoproteins with molecular weights of 50-52,000 from gCII-93 and gCII-200 appeared to be the same glycoprotein since they could be immunoprecipitated by 9E10 and had identical peptide maps. The amino sugar content of these glycoproteins was compared to that of higher molecular weight glycoproteins obtained from gCII-200 and to a glycoprotein with a molecular weight of 93,000 (gp93(I)) from gCI.

Glycoproteins with molecular weights of 50-52,000 derived from both gCII-93 and gCII-200 contained similar amounts of galactosamine (GalN), glycosamine (GlcN) and sialic acid. Also, they both contained 2-3 times more GalN than any other glycoprotein from gCII-200 and 10 times more GalN than was detected in gp93(I). All glycoproteins from gCII-93 or gCII-200 also contained more sialic acid when compared to gp93(I). GalN in these glycoproteins was present in O-linked oligosaccharides. This was demonstrated by release of low molecular weight oligosaccharides from the high molecular weight glycopeptides by mild base hydrolysis and the conversion of GalN to galactosaminitol. Thus, gp52(II) appears to have a unique phenotype marked by a high amount of O-linked oligosaccharides.

A summary of the various abbreviations employed to refer to these two types of glycoprotein complexes, their constituent glycoproteins and the monoclonal antibodies used to immunoprecipitate them appears on Table A, below.

TABLE A

HCMV Envelope Glycoprotein Complexes and Glycoproteins

| Glycoprotein Complex (m.w. in kD) | Glycoprotein Component(s) (m.w. in kD) | Recognized by Monoclonal Antibodies |
|---|---|---|
| gA or gCI (130-190) | GLP-A[1] (55),(93),(130) | 41C2 (ATCC HB 10927),[5] 9B7 (ATCC HB 10925)[5] |
| gB or gCII (93),[3](>200)[4] | GLP-B[1] (50-52), (90),(200)[2] | 9E10(ATCC HB 10926)[5] 12G9, 14F9, 15F9 (ATCC HB 10930)[5] |

[1] Designation in commonly-assigned U.S. application Serial No. 933,789 now abandoned, the entire disclosure of which is incorporated by reference herein; the 93 kD glycoprotein is designated gp93(I) herein.
[2] gp52(II), gp90(II) and gp200(11), respectively, herein.
[3] gCII-93 herein.
[4] gCII-200 herein.
[5] American Type Culture Collection (ATCC), Rockville, Maryland, USA, accession number.

BRIEF DESCRIPTION OF THE DRAWINGS

FIGS. 2A-2C are profiles of glycoproteins obtained by immunoprecipitation of the gCI complex (3UR) with monoclonal antibody 41C2, and the gCII complexes (gCII-93 (2UR); gCII-200 (4UR) with monoclonal antibody 9E10. Each of the immunoprecipitated complexes were solubilized in sodium dodecyl sulphate (SDS), reduced with dithiothreitol (DTT), alkylated with iodoacetamide, and then separated by gel-filtration HPLC.

FIG. 2A is the resolution peak of a 93,000 molecular weight glycoprotein (gp93(I)), obtained from reducing the immunoprecipitated gCI complex (3UR) and separating the material by gel filtration HPLC.

FIG. 2B is the resolution peaks of (1) a 90,000 molecular weight glycoprotein (gp90 (II-93)), and (2) a 50-52,000 molecular weight glycoprotein (gp52 (II-93)), obtained from reducing the immunoprecipitated gCII-93 complex (2UR) and separating the material by gel filtration HPLC.

FIG. 2C is the resolution peaks of (1) a greater than 200,000 molecular weight glycoprotein (gp200 (II-200)), (2) a 90,000 to 200,000 molecular weight glycoprotein (gp90 (II-200)), and (3) a 50-52,000 molecular weight glycoprotein (gp52 (II-200)), obtained from reducing the immunoprecipitated gCII-200 complex (4UR) and separating the material by gel filtration HPLC.

DETAILED DESCRIPTION OF THE INVENTION

A. Materials and Methods

Figure 1:
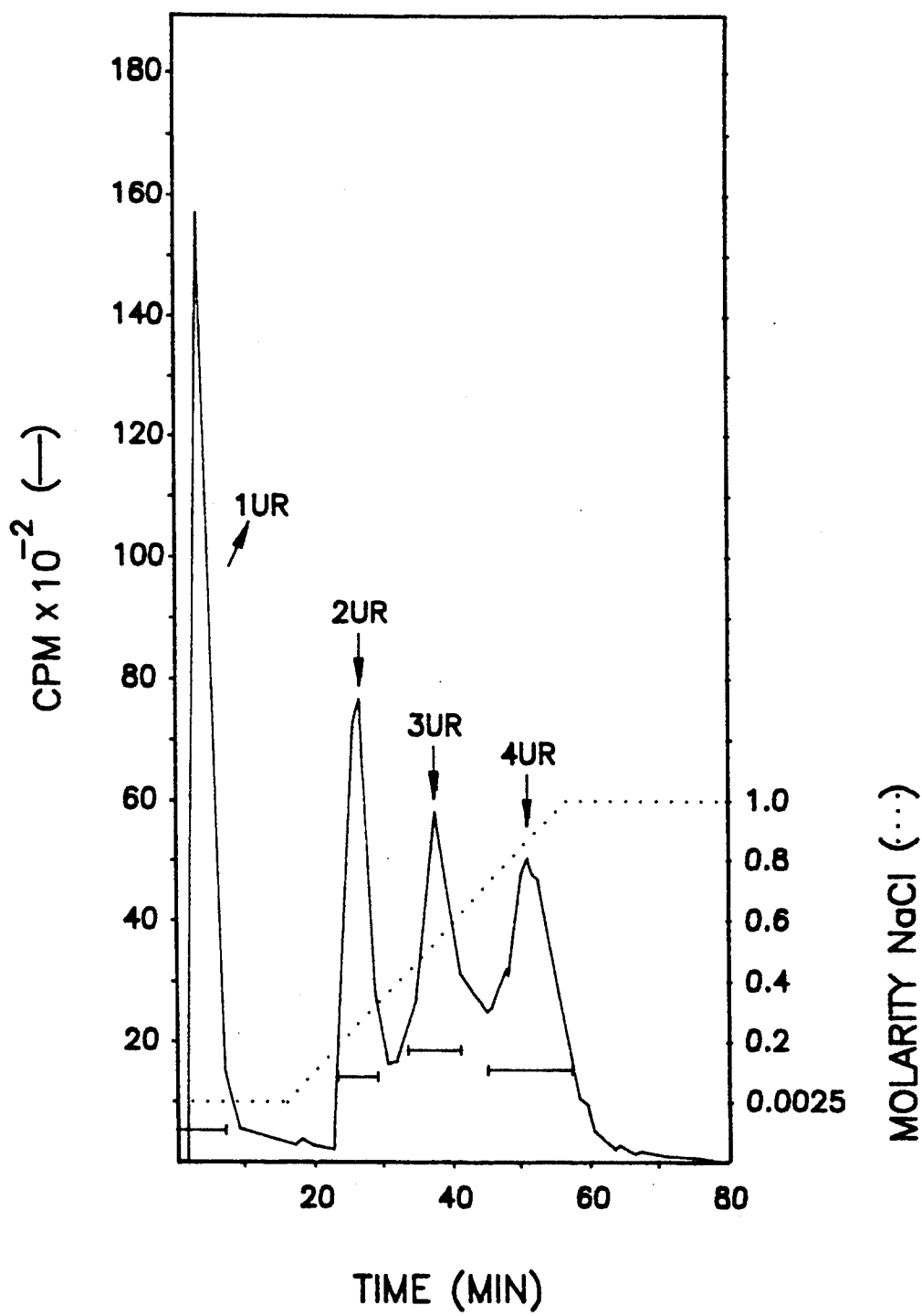
FIG. 1 is a profile of radioactivity of unreduced HCMV glycoprotein complexes obtained from a nonionic detergent extract of labeled, purified HCMV virus that was applied to an anion-exchange HPLC column. (1UR = material containing glycoplipid; 2UR = gCII-93 complex; 3UR = gCI complexes; 4UR = gCII-200 complex).

1. Monoclonal antibodies Production and characterization of monoclonal antibodies used in these studies have been previously described by B. E. Kari et al., *J.*

*Virol.*, 60, 345 (1986), the disclosure of which is incorporated by reference herein.

Spleen cells from mice immunized with purified Towne strain HCMV were fused with SP-2-O-Ag14 myeloma cells. The fused cells were screened to detect those which were positive for gCII. To do this, gCII was initially purified by ion-exchange HPLC as previously described (Kari et al., *J. Virol.*, 60, 345 (1986). The gCII purified by HPLC contained a small amount of gCI. The contaminating gCI was removed by immunoprecipitation with a gCI-specific monoclonal antibody. Finally, the highly purified gCII was adsorbed to 96 well plates which were used in an ELISA assay to screen culture media obtained from the fusion cultures. Cells reactive with gCII were subcloned by limiting dilution.

Clonality of monoclonal antibodies 41C2 and 9E10 was established by twice subcloning each antibody. Furthermore, each antibody had an individual isotype (41C2 was a IgG1 and 9E10 was a IgG3) and each appears as an individual antibody by isoelectric focusing.

2. Purification of HCMV glycoproteins Labeling of Towne strain HCMV with [$^3$H]glucosamine or with [$^{14}$C]glucosamine and [$^3$H]arginine, collection of extracellular virus, nonionic detergent extraction of glycoprotein complexes, and anion-exchange HPLC were done as previously described by B. E. Kari et al., cited above. Complexes designated gCII-93 and gCII-200 were immunoprecipitated with monoclonal antibody 9E10 and complex gCI was immunoprecipitated with monoclonal antibody 41C2 using protein A sepharose.

The immunoprecipitated complexes were solubilized by heating them at 60° C. for 5 min. in Tris buffer (pH 8) containing 4% SDS. After cooling, urea was added to a final concentration of 8M and complexes reduced with 10 mM dithiothreitol (DTT) at room temperature for 4 hrs before adding iodoacetamide. Alkylation was allowed to proceed for 2 hrs at room temperature. Samples were dialyzed against 0.1% SDS and reduced in volume to 0.5 ml.

Individual glycoproteins were separated by gel-filtration HPLC using coupled columns of TSK 3000 and 4000 (Toyo Soda, Japan). HPLC was done at a flow rate of 0.3 ml/min. using a buffer of 10 mM Tris (pH 7.8) containing 0.1% SDS. Eluate was monitored for radioactivity.

3. Immunoaffinity purification of gCII To obtain gCII for Western blot analysis, an immunoaffinity method was used. A gCII-specific monoclonal antibody (15F9) was biotinylated according to the method of Gretch et al., *Anal. Biochem.*, 163, 270 (1987). Biotinylated 15F9 was reacted with a 1.0% nonidet P-40 (Sigma Chem. Co.) extract of HCMV which contained gCII. The antibody antigen complex was immunoprecipitated by using streptavidin agarose. The agarose antibody complex was washed with phosphate buffered saline containing 0.1% nonidet P-40. After washing, gCII was eluted from the agarose antibody complex by heating at 100° C. for 3 min. in a Tris buffer (0.2M Tris, pH 6.8, containing 6% SDS).

4. Western blot analysis of gCII using murine monoclonal antibodies and human sera positive for HCMV Purified gCII was reduced with betamercaptoethanol (BME) and individual glycoproteins separated by electrophoresis in 10% polyacrylamide gels. Western blot was done as previously described (Lussenhop et al., *Virology*, 164, 362–372 (1988)). Human sera was used at a dilution of 1:30 and monoclonal antibodies were used at a dilution of 1:500.

5. Immunoprecipitation and immunofluorescence Immunoprecipitations and immunofluorescence were done as previously described (Kari et al., *J. Virol.*, 60, 345–352 (1986)). For immunoprecipitations, nonidet P-40 extracts of [$^3$H]GlcN or [$^{14}$C]GlcN labeled HCMV were used.

6. SDS-PAGE and fluorography SDS-PAGE was done with 5–15% polyacrylamide slab gel gradients following the method of U. K. Laemmli, *Nature*, 227, 680 (1970). Tritium in gels was detected by fluorography using Enlighting (New England Nuclear Corp., Boston, MA).

7. Pronase digestion Pronase (Calbiochem) digestion was done at 60° C. for 48 hrs as previously described by F. Dall'Olio et al., *J. Virol.*, 56, 127 (1985), with the exception that 0.1% SDS was used and enzyme was added twice to a final concentration of 0.3%. After pronase digestion detergent was removed using Extracti-Gel D (Pierce Chem. Co., Rockford, IL).

8. G-50 column chromatography Chromatography of pronase glycopeptides was done using a Sephadex G-50 column (1×50 cm) equilibrated with 0.1N acetic acid. The void volume (Vo) was determined with blue dextran and the total included volume (Vt) with [$^3$H]glucosamine. The elution volume of N-linked complex and high mannose glycopeptides was accomplished as previously described by S. Olofsson et al., *J. Gen. Virol.*, 64, 6735 (1983).

9. Identification of sialic acid Glycopeptides obtained from G-50 chromatography were digested with 0.1 U of neuraminidase (Sigma Chem. Co., St. Louis, MO) in 0.1M acetate buffer (pH 5) containing 10 mM $CaCl_2$ at 37° C. for 24 hrs. Samples were applied to a Dowex 1 column in the formate form. The column was washed with 3 column volumes of water to remove unbound label and then with 2N formate to release sialic acid. Label released with 2N formate was further characterized by paper chromatography using n-butanol:water:acetic acid (120:50:30, v/v/v) as the solvent system (solvent A). Radioactive sialic acid standard and label released by 2N formate was detected by cutting lanes into 1 cm strips and detecting radioactivity by liquid scintillation.

10. Strong acid hydrolysis for determination of hexosamines Prior to hydrolysis samples were desalted on P6-DG (Bio Rad). For smaller glycopeptides eluting near the Vt of the G-50 column desalting was done with coupled columns of Dowex 50 (H$^+$) and Dowex 1 (OH$^-$) as previously reported by R. G. Spiro, *Methods Enzymol.*, 28, 3 (1972). Desalted glycopeptides were hydrolyzed in 4N HCl for 4 hrs at 100° C. in a final volume of 1 ml and dried under vacuum. N-acetylgalactosaminitol (GalNAc-ol) was prepared following the method of W. R. C. Crimmin, *J. Chem. Soc.*, 2838 (1957). GalNAc-ol and all other standards were hydrolyzed so that deacetylated forms were subjected to TLC.

11. Mild alkaline borohydride treatment Alkaline borohydride treatment of pronase glycopeptides was done by the method of R. G. Spiro, cited above.

12. TLC Thin layer chromatography (TLC) was carried out according to the methods of Dall'Olio et al., cited above, using silica gel 60 on plastic-backed plates from Merck. The solvent system was ethanol:pyridine:1-butanol:acetic acid:water (100:10:10:3:30, v/v/v/v/v) to which 1% (w/v) potassium tetraborate was added (solvent B). Radioactive hexosamines were detected by fluorography using Enhance spray (New England Nuclear Corp., Boston, MA) and quantitated by densitometric scans of fluorograms. Non-radioactive standards were run in lanes adjacent to the unknowns. After development of TLC plates, lanes containing standards were cut from the plates and hexosamines detected with ninhydrin spray.

13. Peptide mapping HCMV glycoproteins double labeled with [$^3$H]arginine and [$^{14}$C]glucosamine were digested with insoluble trypsin (Sigma Chem. Co., St. Louis, MO) in Tris buffer (pH 7.8) containing 0.1% SDS for 24 hrs at room temperature with constant mixing. The peptides obtained were separated by gel-filtration HPLC as described above.

14. DEAE ion-exchange and affinity chromatography DEAE chromatography was done as previously described by F. Serafini-Cessi et al., *Biochem. J.*, 215, 483 (1983) using a DEAE-sepharose (fast flow, Pharmacia) column (1×10 cm). The elution position of a monosialylated oligosaccharide was determined using sialyllactose (Sigma Chem. Co., St. Louis, MO) which was detected by the phenol sulfuric acid assay. Wheat germ agglutinin (WGA) and peanut lectin affinity media were obtained from United States Biochemical Co. Chromatography was done with 1 ml columns. Samples were allowed to adsorb onto the columns for 10 min. before washing with 15 bed volumes of appropriate buffer. Bound material was eluted with the appropriate monosaccharide.

B. Results

1. Purification of HCMV complexes and glycoproteins Glycoprotein complexes were extracted from purified virus labeled with [$^3$H]GlcN using conditions which are known to solubilize the membrane, but not the nucleocapsid [G. H. Farrar et al., *J. Gen. Virol.*, 65, 1991 (1984)]. As depicted in FIG. 1, fractionation of these extracts by ion-exchange HPLC using a linear gradient of NaCl, generated 4 peaks when glycoproteins were labeled with [$^3$H]GlcN. One peak was not retained by the column. The material in this peak could not be fixed in polyacrylamide gels under conditions which fix proteins, could not be labeled with [$^{35}$S]methionine, and was soluble in chloroform methanol (2:1). Based on these observations, it was concluded that this peak contained glycolipid.

The three retained peaks depicted in FIG. 1 contained several disulfide-linked glycoprotein complexes. Peaks 2UR and 4UR contained complexes gCII-93 and gCII-200, respectively, which were recognized by monoclonal antibody 9E10. After reduction of disulfide bonds, gCII-93 generated glycoproteins with molecular weights of 90,000 and 50–52,000, while gCII-200 generated glycoproteins ranging in molecular weight from 50–52,000 to greater than 200,000. Peak 3UR contained gCI complexes, which were recognized by monoclonal antibody 41C2. After reduction of disulfide bonds, gCI generated glycoproteins with molecular weights of 130,000, 93,000 and 50,000. Peak 2UR also contained a 93,000 molecular weight glycoprotein which was not disulfide-linked to other glycoproteins and was not immunoprecipitated by the monoclonal antibodies. This glycoprotein was not examined further.

Glycoprotein complexes gCII-93 and gCII-200 were immunoprecipitated with 9E10 and gCI was immunoprecipitated with 41C2. Immunoprecipitated complexes were solubilized in SDS, reduced with DTT, alkylated with iodoacetamide, and the individual glycoproteins were separated by gel-filtration HPLC. By gel-filtration, we were able to obtain a 93,000 molecular weight glycoprotein (designated gp93 (I)) from gCI (FIG. 2A).

Material from gCII-93 was resolved into two peaks (FIG. 2B). A minor peak contained a 90,000 molecular weight glycoprotein (gp90(II)), while a second major peak had a glycoprotein with a molecular weight of 50–52,000 (designated gp52(II-93)), for purposes of comparison of the material with the corresponding glycoprotein derived from gCII-200.

After reduction of disulfide bonds, gCII-200 resolved into at least 3 peaks (FIG. 2C). The first peak contained material with a molecular weight greater than 200,000 (designated gp200(II)); the second peak contained a smear of material ranging in molecular weight from 90,000 to 200,000 (designated gp90(II)) (FIG. 2C). The third peak was the most abundant when glycoproteins were labeled with [$^3$H]GlcN. This peak containing glycoproteins with molecular weights of 50–52,000 (designated gp52(II-200)) (FIG. 2C).

2. Immunoprecipitation and peptide mapping of gp52 (II-93) and gp52(II-200) The glycoproteins in glycoprotein complexes gCII-93 and gCII-200 are immunoprecipitated by 9E10 after reduction of disulfide bonds and appear to be immunologically-related. The relationship between these glycoproteins, gp52(II-93) and gp52(II-200), was examined by re-immunoprecipitating each as a purified glycoprotein with 9E10 and by peptide mapping. Both purified glycoproteins could be immunoprecipitated by 9E10, further establishing their immunological relationship. For peptide mapping, glycoproteins were double labeled with [$^3$H]arginine and [$^{14}$C]GlcN. Glycoprotein 93 (I) was examined for comparison.

The purified glycoproteins were digested with trypsin and fragments separated by gel-filtration HPLC. By this method, three major peptides were obtained from gp93(I). All three contained carbohydrate, suggesting that gp93(I) contains at least three glycosylation sites. With gp52(II-93) and gp52(II-200), two major fragments were obtained. One eluted with a molecular weight of approximately 30,000 and contained most of the [$^{14}$C]GlcN. A second fragment had a molecular weight of approximately 10,000 and contained little or no [$^{14}$C]GlcN. Smaller, less abundant peaks were also detected. With both glycoproteins, the most abundant of these eluted with arginine.

3. Characterization of monoclonal antibodies 9E10 and 15F9

(a) Immunofluorescence.

Antibodies were screened by immunofluorescence using fibroblasts which were infected with either Towne strain HCMV, HSV, VSV or adenovirus. MoAb 9E10 was positive for HCMV Towne strain and was also positive for HSV and adenovirus.

(b) Immunoprecipitation of radioactively labeled gCII from HCMV strains Towne and AD169.

Towne and AD169 strains of HCMV were grown with radioactive GlcN. Purified virus was extracted with 1% nonidet P-40. These extracts were used for immunoprecipitation. Monoclonal antibody 9E10 immunoprecipitated gCII from Towne strain HCMV, but not strain AD169. Monoclonal antibody 15F9 immunoprecipitated gCII from HCMV strains Towne and AD169.

(c) Western blot analysis of immunoaffinity purified gCII.

After purification, gCII was reduced with beta-mercaptoethanol and individual proteins separated by gel electrophoresis in 10% polyacrylamide gels. Separated proteins were electroblotted onto nitrocellulose paper. Electroblotted proteins were reacted with monoclonal antibodies 9E10 and 15F9 and several human sera. Monoclonal antibody 9E10 reacted most strongly with proteins with molecular weights from 45 to 63,000 [these include gp52(II) derived from gpII(200) (gp52(II-200)) which is immunoprecipitated by 9E10] (FIG. 2).

Monoclonal antibody 15F9 reacted strongly with proteins derived from reduced gpII(200), which have molecular weights of 50 to 52,000 (gp52(II-200)), 90,000 (gp90(II-200)), and greater than 200,000 (gp200(II-200)).

None of these glycoproteins is recognized by human sera negative for HCMV. However, several positive human sera recognize the same glycoproteins as 15F9, suggesting that these glycoproteins (gp90(II-200)) and gp200(II-200)) are important in human immune recognition of HCMV. Finally, a known protein with a molecular weight of 28,000 was also recognized by the human sera. This protein was recognized by 35F10 which is specific to HCMV, but does not recognize gCII. It is likely that this protein is a contaminant of the gCII preparation.

4. Analysis of HCMV glycoproteins for amino sugar content The purified glycoproteins from Towne strain HCMV were analyzed to determine their amino sugar content. These studies were done with [$^3$H]GlcN labeled glycoproteins. When [$^3$H]GlcN is used, protein-bound radioactivity can be found in GlcN, GalN and sialic acid, allowing detection and quantitation of these amino sugars. Labeled glycoproteins were digested with pronase and glycopeptides were separated by G-50 chromatography. The separated glycopeptides were subjected to neuraminidase digestion prior to strong acid hydrolysis to quantitate the amount of sialic acid present. Radioactivity released by neuraminidase was bound to a Dowex 1 column in the formate form and was released by 2N formate. In addition, label eluting with 2N formate co-migrated with authentic sialic acid with paper chromatography using solvent system A. The amount of radioactivity released by neuraminidase was used to quantitate the amount of sialic acid in the various glycoproteins. To quantitate the amount of GlcN and GalN, desialylated glycopeptides were subjected to strong acid hydrolysis and hexosamines separated by TLC.

Separation of pronase glycopeptides from gp93 (I) by G-50 chromatography generated a minor peak which eluted near the Vo. This peak contained GalN and GlcN. However, with gp93 (I), most of the glycopeptides were found in the partially included volume, eluting with N-linked glycopeptide standards. Ninety eight percent of the radioactivity in this peak was incorporated as GlcN. Quantitation of radioactivity in all amino sugars in gp93 (I) showed that 86% of the radioactivity was in the form of GlcN (Table B).

TABLE B

| Glycoprotein | Distribution of Radioactivity in Sialic Acid, GlcN and GalN | | |
|---|---|---|---|
| | Sialic Acid (a) (%) | GlcN (b) (%) | GalN (%) |
| qp93(I) | 9 | 86 | 5 |
| qp200(II) | 13 | 73 | 14 |
| gp90(II) | 14 | 69 | 16 |
| gp52(II-200) | 15 | 38 | 47 |
| gp52(II-93) | 14 | 47 | 39 |

(a) Each G-50 peak was treated with neuraminidase and the reaction mixture applied to a Dowex 1 column in the formate form. The radioactivity which bound to the column was eluted with 2 N formate. This amount of radioactivity was divided by the total amount of radioactivity applied to obtain the percentage of radioactivity in the form of sialic acid.
(b) The material from each G-50 peak which did not bind to the formate column was subjected to acid hydrolysis to obtain individual hexosamines. Hexosamines were separated by TLC and detected by fluorography. The relative amount of radioactivity in the form of GlcN and GalN was determined by scanning the fluorograms. These values were multiplied by the fractional amount of neutral radioactivity in each G-50 peak.

The data summarized on Table B suggests the gp93(I) contains largely N-linked oligosaccharides.

After pronase digest, glycopeptides from gp52 (II-93) and gp52(II-200) were resolved into three peaks by G-50 chromatography. The first peak eluted at the Vo. Material in this peak was collected and redigested with pronase for 24 hrs with no further degradation. The glycopeptides eluting at the Vo may have contained closely spaced oligosaccharides on the peptide backbone which can prevent the action of pronase. While G-50 peak 1 from both gp52(II-93) and gp52(II-200) contained 72-75% GalN, the peak itself was more abundant in gp52(II-200). The second peak (G-50 peak 2) eluted with N-linked standards and contained 82-91% GlcN, indicating the presence of N-linked oligosaccharides in these glycoproteins. The third peak (G-50 peak 3) eluted near the Vt and contained similar amounts of GlcN and GalN.

Both gp90(II) and gp200(II) were examined in the same manner as gp52(II-200). The results from these experiments were used to quantitate the relative amount of radioactivity incorporated in the different amino sugars (Table B). The relative amount of radioactivity found in the form of sialic acid in glycoproteins from gCII-93 and gCII-200 was very similar, but significantly greater than that detected in gp93(I) (Table B). Moreover, all glycoproteins from gCII-93 and gCII-200 contained more GalN than gp93(I). However, gp52 from both gCII complexes contained two to three times more GalN than other glycoproteins from the same complexes.

5. Analysis of glycopeptides obtained after mild alkaline borohydride treatment Since glycoproteins from gCII-93 and gCII-200 contained high amounts of GalN, it was of interest to determine if the GalN was present in O-linked oligosaccharides. To determine this, the glycopeptides were subjected to the beta-elimination reaction which cleaves oligosaccharides which are O-glycosidically-linked to serine or threonine. N-acetylgalactosamine, which is usually present at the reducing end of the oligosaccharide, is converted to GalNAc-ol. Oligosaccharides obtained after beta-elimination were subjected to strong acid hydrolysis and hexosamines examined to demonstrate the conversion of GalN to GalN-ol.

When glycopeptides in the G-50 peak 1 of gC-II glycoproteins were re-chromatographed on G-50 after beta-elimination, there was a shift from the Vo to near the Vt. The molecular weight of this material was approximately 1500. This result was obtained with all glycoproteins from gCII-93 or gCII-200. There was also material which eluted earlier as a small peak or shoulder. Material eluting early contained GlcN, indicating it contained N-linked oligosaccharides, while material eluting near the Vt co-migrated with GalN-ol. A small amount of radioactivity in the Vt peak migrated in front of the GlcN standard. This fast migrating material was most likely degradation products obtained by strong acid hydrolysis of GalN-ol. The elution position of G-50 peak 2 was not affected by the beta-elimination reaction carried out on any glycoprotein from gCI, gCII-93 and gCII-200. This peak contained GlcN, demonstrating that the oligosaccharides were N-linked. The elution position of G-50 peak 3 from any glycoprotein from gCII-93 or gCII-200 was not affected by beta-elimination, but GalN in this peak was converted to GalN-ol. This suggested that the GalN in this peak was O-glycosidically linked.

6. Degree of sialylation and terminal sugar residues of O-linked oligosaccharides The oligosaccharides from gp52(II-93) and gp52(II-200) were examined to measure their degree of sialylation. These studies were confined to glycopeptides from G-50 peak 1 since it contained most of the O-linked oligosaccharides. For these studies, gCII-93 and gCII-200 were immunoprecipitated directly from detergent extracts without prior separation by ion-exchange chromatography. By this method, gp52(II-93) and gp52(II-200) were isolated as one glycoprotein designated gp52(II).

By DEAE chromatography, glycopeptides in G-50 peak 1 were resolved into three peaks. Of the applied radioactivity, 17% was not retained by the column. As determined by TLC, this peak contained only GalN, suggesting that some O-linked oligosaccharides were neutral and did not contain sialic acid. Peak 2 eluted at a salt concentration needed to elute a monosialylated oligosaccharide and contained 96% GalN. This suggested the presence of O-linked oligosaccharides containing a single sialic acid residue. Most of the GlcN in G-50 peak 1 was detected in peaks 3 and 4, but these peaks still contained 85% GalN, suggesting that some O-linked oligosaccharides contained more than one sialic acid residue. The uneven distribution of hexosamines in the DEAE peaks suggested that glycopeptides containing N- and O-linked oligosaccharides were binding independently or that there were different glycopeptides, some with only O-linked oligosaccharides and some with N- and O-linked oligosaccharides.

To determine the nature of the non-reducing terminal monosaccharides in glycopeptides from G-50 peak 1, a series of lectin affinity columns were used. Most of the glycopeptides from G-50 peak 1 were retained by the DEAE column, indicating that they contained sialic acid. Therefore, glycopeptides were applied to a WGA column which has affinity for non-reducing terminal sialic acid and GlcNAc residues [K. Yamamoto et al., *Biochemistry*, 20, 5894 (1981)]. When this was done, 85% of the radioactivity bound to the column. Taken together, DEAE and WGA affinity chromatography suggest that these glycopeptides contain non-reducing terminal sialic acid residues.

The portion which did not bind WGA would contain the neutral glycopeptides detected by DEAE chromatography. These glycopeptides were applied to a peanut lectin column which has strong affinity for the structure Gal-GalNAc [I. J. Goldstein et al., Advances in Carbohydrate Chemistry and Biochemistry, Academic Press, NY, 35, 127–340 (1978)]. Of the radioactivity applied, 58% bound and was eluted with 0.05M Gal, indicating that O-linked oligosaccharides were present which had Gal as a terminal residue. Furthermore, since sialic acid is often the terminal sugar linked to the penultimate residue Gal of both N- and O-linked oligosaccharides, it was of interest to treat that portion which originally bound to WGA with neuraminidase to remove sialic acid. Prior to neuraminidase treatment, less than 10% of the radioactivity which bound WGA had affinity for peanut lectin. After neuraminidase treatment, 81% of the radioactivity bound to the column and was eluted with Gal. This result is consistent with the interpretation that oligosaccharides in this fraction have a terminal sialic acid residue and a penultimate Gal residue.

C. Discussion

While there have been a number of reports characterizing gC-I and its glycoproteins, there have been no reports other than Kari et al., cited above, describing gCII, its glycoproteins or monoclonal antibodies reactive therewith. Based upon the studies reported hereinabove, the 50–52,000 molecular weight glycoproteins in gCII-93 and gCII-200 appear to be the same glycoprotein. This conclusion is based on several observations.

First, they have the same molecular weight in SDS-PAGE and are immunoprecipitated by the same monoclonal antibody (9E10). They also had identical peptide maps and the amino sugar content of pronase glycopeptides was similar. The major difference between gp52(II-93) and gp52(II-200) appears to be their association in different disulfide-linked complexes. Glycoproteins present in multimeric forms in viral membranes is not unprecedented. For example, glycoprotein C has been detected in multimeric forms in HSV-2. Of the two glycoprotein complexes which we detected, gCII-200 appears to be more abundant based on ionexchange HPLC data. Therefore, glycoproteins gp52(II-93) and gp52(II-200) were collectively designated gp52(II).

All of the HCMV Towne strain glycoproteins which we isolated contained N-linked oligosaccharides. These were identified as N-linked by several criteria. First, they co-eluted with N-linked standards on gelfiltration and contained high amounts of GlcN. Moreover, GlcN was still detected after mild alkaline treatment and their elution position did not change. The N-linked oligosaccharides were not examined further.

Very few viral glycoproteins have been characterized which contain high amounts of O-linked oligosaccharides. Of the HCMV glycoproteins characterized, O-linked oligosaccharides were most abundant in gp52(II). It appears that gp52(II) contains a cluster of hydroxyamino acids to which some of the O-linked oligosaccharides are bound. This is based on the observation that pronase resistant high molecular weight glycopeptides containing high amounts of GalN were always obtained. The nearly complete conversion of the GalN in this fragment to GalN-ol indicated that most of the GalN was at the reducing end of the oligosaccharide attached to either serine or threonine. Thus, this fragment would have to contain a number of hydroxy-amino acids.

The O-linked oligosaccharides of gp52(II) appear to be terminated by at least Gal and sialic acid. Neutral O-linked oligosaccharides were detected by DEAE chromatography. Among the neutral oligosaccharides were those apparently terminated by Gal as determined by their affinity for peanut lectin. However, of the glycopeptides tested, most bound DEAE and required pretreatment with neuraminidase to bind peanut lectin. These results suggested that some O-linked oligosaccharides were terminated with Gal, but in others, sialic acid was the terminal residue and Gal the penultimate. It is also possible, based on DEAE data, that some of the O-linked oligosaccharides contained more than 1 sialic acid residue.

Our results also show that gp52(II) contains a high content of Gal and GalNAc. Farrar and Oram, *J. Gen. Virol.*, 65, 1991 (1984), also found glycoproteins in HCMV strain AD169 which had high amounts of Gal and/or GalNAc. However, the lowest molecular weight they reported for a glycoprotein with these characteristics was 67,000.

We found the molecular weights of the O-linked oligosaccharides to be approximately 1500 after beta-elimination. However, the presence of sialic acid in an oligosaccharide can increase its apparent molecular weight in gel-filtration. Thus, the molecular weights of these oligosaccharides may actually be less. Glycoproteins which normally contain O-linked oligosaccharides in this molecular weight range include the proteoglycans, immunoglobulin light chains and MN blood group glycoprotein. These oligosaccharides contain GalNAc, Gal, and 1 to 2 sialic acid residues. Sialic acid in most of these oligosaccharides is the nonreducing terminal monosaccharide while Gal is the penultimate. Thus, it seems that the enzymes involved in the synthesis of these oligosaccharides must be active in cells infected by HCMV.

The following monoclonal antibodies have been placed on deposit at American Type Culture Collection (ATCC), 12301 Parklawn Drive, Rockville, Md., 20852 under the accession numbers as indicated (original dates of deposit of Sep. 10, 1986 for monoclonal antibodies 9E10, 41C2 and 9B7; and Jul. 31, 1988 for monoclonal antibody 15F9):

| Monoclonal Antibody | Accession No. |
|---|---|
| 9E10 | ATCC HB 10926 |
| 41C2 | ATCC HB 10927 |
| 15F9 | ATCC HB 10930 |
| 9B7 | ATCC HB 10925 |

The invention has been described with reference to various specific and preferred embodiments and techniques. However, it should be understood that many variations and modifications may be made while remaining within the spirit and scope of the invention.

What is claimed is:

1. A substantially-pure, immunogenic glycoprotein complex which is derivable from the membrane envelope of human cytomegalovirus, has a molecular weight as determined by SDS-PAGE technique of greater than about 200 kDa, and has as reduced disulfide subunits at least three glycoproteins that have molecular weights of about 50 to 52 kDa, about 90 kDa, and about 200 kDa as determined by SDS-PAGE technique, the subunit glycoproteins being associated with each other in said complex by means of at least one disulfide bond;

said complex with disulfide bond or bonds intact being immunoreactable with monoclonal antibody 9E10 produced by hybridoma ATCC HB 10926 or monoclonal antibody 15F9 produced by hybridoma ATCC HB 10930, but not with monoclonal antibody 41C2 produced by hybridoma ATCC HB 10927.

2. The glycoprotein complex according to claim 1, wherein the reduced disulfide subunit glycoproteins with molecular weights of about 90 kDa and about 200 kDa are immunoreactable with monoclonal antibody 15F9 but not with monoclonal antibody 9E10 or 41C2.

3. A substantially pure immunogenic glycoprotein which has a molecular weight as determined by SDS-PAGE technique of about 90 kDa, has at least one sulfhydryl group, is derivable from a substantially pure immunogenic glycoprotein complex having a molecular weight as determined by SDS-PAGE technique of greater than about 200 kDa, which complex is obtained from the membrane envelope of human cytomegalovirus, and, when within said complex, the glycoprotein is a subunit glycoprotein associated by means of at least one disulfide bond with other subunit glycoproteins having molecular weights of about 50 to 52 kDa and about 200 kDa, as determined by SDS-PAGE technique; the greater than about 200 kDa complex with disulfide bond or bonds intact being immunoreactable with monoclonal antibody 9E10 or 15F9, but not with monoclonal antibody 41C2.

4. The about 90 kDa glycoprotein according to claim 3, which is immunoreactable with monoclonal antibody 15F9 but not with monoclonal antibody 9E10 or 41C2.

5. A substantially pure immunogenic glycoprotein which has a molecular weight as determined by SDS-PAGE technique of about 200 kDa, has at least one sulfhydryl group, is derivable from a substantially pure immunogenic glycoprotein complex having a molecular weight as determined by SDS-PAGE technique of greater than about 200 kDa, which complex is obtained from the membrane envelope of human cytomegalovirus, and, when within said complex, the glycoprotein is a subunit glycoprotein associated by means of at least one disulfide bond with other subunit glycoproteins having molecular weights of about 50 to 52 kDa and about 200 kDa, as determined by SDS-PAGE technique; the greater than about 200 kDa complex with disulfide bond or bonds intact being immunoreactable with monoclonal antibody 9E10 produced by hybridoma ATCC HB 10926 or monoclonal antibody 15F9 produced by hybridoma ATCC HB 10930, but not with monoclonal antibody 41C2 produced by hybridoma ATCC HB 10927.

6. The about 200 kDa glycoprotein according to claim 5, which is immunoreactable with monoclonal antibody 15F9 but not with monoclonal antibody 9E10 or 41C2.

7. A substantially pure immunogenic glycoprotein which has a molecular weight as determined by SDS-PAGE technique of about 50 to 52 kDa, has at least one sulfhydryl group, is derivable from a substantially pure immunogenic glycoprotein complex having a molecular weight as determined by SDS-PAGE technique of greater than about 200 kDa, which complex is obtained from the membrane envelope of human cytomegalovirus, and, when within said complex, the glycoprotein is a subunit glycoprotein associated by means of at least one disulfide bond with other subunit glycoproteins having molecular weights of about 90 kDa and about 200 kDa, as determined by SDS-PAGE technique; the greater than about 200 kDa complex with disulfide bond or bonds intact being immunoreactable with monoclonal antibody 9E10 produced by hybridoma ATCC HB 10926 or monoclonal antibody 15F9 produced by hybridoma ATCC HB 10930, but not with monoclonal antibody 41C2 produced by hybridoma ATCC HB 10927.

8. The about 50 to 52 kDa glycoprotein according to claim 7, which is immunoreactable with monoclonal antibody 9E10 but not with monoclonal antibody 15F9 or 41C2.

9. The glycoprotein of claim 3 or 5 or 7 which is produced by a process comprising reducing the disulfide linkages of a substantially pure, immunogenic glycoprotein complex which is derivable from the membrane envelope of human cytomegalovirus, and has a molecular weight as determined by SDS-PAGE technique of greater than about 200 kDa.

* * * * *

UNITED STATES PATENT AND TRADEMARK OFFICE
CERTIFICATE OF CORRECTION

PATENT NO. :
DATED      :     5,153,311
INVENTOR(S) :    October 6, 1992

Bruce E. Kari et al.

It is certified that error appears in the above-identified patent and that said Letters Patent is hereby corrected as shown below:

At column 9, in Table B at line 66 for "qp93(I) read --gp93(I)--.

At column 9, in Table B at line 67 for "qp200(II) read --gp200(II)--.

Signed and Sealed this

Nineteenth Day of July, 1994

Attest:

BRUCE LEHMAN

Attesting Officer        Commissioner of Patents and Trademarks